United States Patent [19]

Molloy

[11] 4,034,011

[45] July 5, 1977

[54] 1,1-DIPHENYL-4-(SUBSTITUTED-AMINO)-BUTANES

[75] Inventor: Bryan B. Molloy, Indianapolis, Ind.

[73] Assignee: Eli Lilly and Company, Indianapolis, Ind.

[22] Filed: Mar. 12, 1976

[21] Appl. No.: 666,278

Related U.S. Application Data

[63] Continuation of Ser. No. 536,284, Dec. 24, 1974, abandoned.

[52] U.S. Cl. .................... 260/570 R; 260/456 A; 260/501.1; 260/501.15; 260/501.21; 260/567.6 M; 424/303; 424/316; 424/329; 424/330
[51] Int. Cl.² ........................................ C07C 87/28
[58] Field of Search ........ 260/570 R, 501.1, 501.21

[56] References Cited

FOREIGN PATENTS OR APPLICATIONS

| 708,771 | 5/1954 | United Kingdom | 260/570 |
| 923,942 | 4/1963 | United Kingdom | 260/570 |
| 1,025,041 | 4/1966 | United Kingdom | 260/570 |

OTHER PUBLICATIONS

Janssen, "Synthetic Analgesics", Part I, Diphenylpropylamines, pp. 13–16 (1968).
Benoit et al., "Chemical Abstracts", vol. 46, pp. 476 (1952).
Morikawa, "Chemical Abstracts", vol. 54, pp. 19588–19589 (1960).
Seidlova et al., "Chemical Abstracts", vol. 62, pp. 11709–11710 (1965).

*Primary Examiner*—Robert V. Hines
*Attorney, Agent, or Firm*—Charles W. Ashbrook; Everet F. Smith

[57] ABSTRACT

Certain 1,1-diphenyl-4-(substituted-amino)butanes are particularly valuable as antiarrhythmic agents.

2 Claims, No Drawings

1,1-DIPHENYL-4-(SUBSTITUTED-AMINO)BUTANES

This is a continuation, of application Ser. No. 536,284, filed Dec. 24, 1974 and now abandoned.

BACKGROUND OF THE INVENTION

This invention relates to certain diphenylbutylamines which have been found to be extremely useful for the treatment of cardiac arrhythmias.

Intense interest has recently developed in drugs which help to control heart arrhythmias due to the severity of heart diseases in general and to the various types of cardiac arrhythmias plaguing mankind. Several N-phenyl-N-indanyl alkylenediamines have recently been prepared and evaluated as antiarrhythmic agents, as described in Canadian Pat. No. 910907. Drugs such as quinidine, procainamide, and lidocaine, have experienced wide usage in the treatment of various arrhythmias, even though severe problems often accompany their usage. For example, toxic doses of quinidine can induce ventricular tachycardia. Procainamide sometimes causes fever, chills, headache, skin rashes, and similar allergic reactions. Like several other antiarrhythmic agents, continued quinidine and procainamide usage may actually precipitate adverse myocardial effects such as ventricular tachycardia and fibrillation.

Research scientists are actively engaged in finding improved antiarrhythmic agents. To this end, certain diphenylalkylamines have now been found to be extremely useful in the treatment of cardiac arrhythmias.

Numerous diphenylalkylamines have been prepared by various investigators and have been shown to be useful as analgesics, anesthetics, antihistamines, antispasmodics, and the like. Janssen, for example, prepared and studied several diphenylpropylamines as analgesics, as described in detail in *Synthetic Analgesics* Part 1, Diphenylpropylamines, Pergamon Press, 1960. Adamson prepared several diphenylbutylamines and diphenylpropylamines and studied their antispasmodic and anesthetic activities, as described in British Pat. No. 624,117. Nowhere has it been taught that diphenylalkylamines might be useful as antiarrhythmic agents. I have now discovered that certain diphenylbutylamines are especially suited to treating cardiac arrhythmias.

An object of this invention is to provide certain compounds useful for the therapeutic and prophylactic treatment of heart arrhythmias.

SUMMARY OF THE INVENTION

The compounds of this invention are 1,1-diphenyl-4-aminobutanes represented by the general structural formula

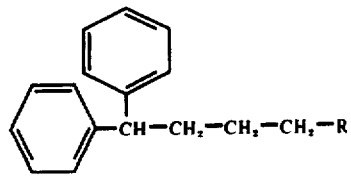

in which R is selected from the group consisting of propylamino, isopropylamino, diisopropylamino, n-butylamino, di-n-butylamino, and tert.-butylamino. The preferred compounds of the invention are those having the above formula wherein R is diisopropylamino or n-butylamino, and R is most advantageously diisopropylamino. Included within the breadth of this invention are the physiologically tolerable salts of the diphenylbutylamines.

DETAILED DESCRIPTION OF THE INVENTION

The compounds of this invention can readily be prepared by any of a number of procedures. For example, an appropriate amine can be condensed with a 1,1-diphenylbutane bearing a displaceable group in the 4-position. More specifically, a 4-halobutane, such as 1,1-diphenyl-4-chlorobutane, can be condensed with an amine, such as diisopropylamine or n-butylamine, thereby forming the corresponding diphenylbutylamine. The reactants are generally employed in about equimolar amounts; however, an excess of either reactant can be utilized if desired. The condensation reaction can best be carried out in a solvent, such as dimethyl sulfoxide, ethyl alcohol, water, benzene, toluene, dichloromethane, or the like. When the reaction is conducted at a temperature of about 20° to 100° C., the product is usually formed after about 2 to 20 hours. The diphenylbutylamine is isolated by removal of the solvent, and further purification such as chromatography or distillation can be carried out if needed.

An alternative method of preparing the diphenylbutylamines of this invention comprises reduction of a 1,1-diphenyl-4-amino-1-butene. The butenes are generally prepared by dehydrating a 1,1-diphenyl-1-hydroxy-4-aminobutane. This method of preparation is described in detail by Adamson, British Pat. No. 624,117.

The compounds of this invention form physiologically tolerable salts with a wide variety of salt forming agents. The most common salts that are generally formed are the acid addition salts. Any of a number of inorganic and organic acids can be utilized in salt formation. While the particular acid selected for salt formation is not critical, the corresponding salt that is formed should be substantially nontoxic to animal organisms. Typical acids most commonly used to form salts include inorganic acids such as hydrochloric, hydrobromic, hydroiodic, sulfuric, phosphoric, sulfamic, nitric, and related acids. Commonly used organic acids include formic acid, acetic acid, butyric acid, succinic acid, oxalic acid, benzoic acid, toluenesulfonic acid, and the like.

Additionally, quaternary ammonium salts can be prepared by reacting a tertiary amine of the invention with an alkylating agent, preferably a $C_1$–$C_4$ alkylating agent. Typical alkylating agents most commonly used include alkyl halides such as methyl chloride, ethyl bromide, propyl iodide, isobutyl iodide, and allyl bromide, or alkyl sulfates such as dimethyl sulfate or diethyl sulfate, and the like. The quaternary ammonium salts are generally prepared by treating a tertiary amine, such as 1,1-diphenyl-4-diisopropylaminobutane, for example, with an alkylating agent in a solvent such as benzene or acetone, and at a temperature of about 20° to 50° C. The quaternary ammonium salts are characteristically highly crystalline solids and are readily isolated by filtration. The quaternary ammonium salts provided herein constitute a group of very important and highly potent antiarrhythmic agents.

Illustrative examples of compounds provided by this invention include:

1,1-Diphenyl-4-propylaminobutane;

1,1-Diphenyl-4-isopropylaminobutane;
1,1-Diphenyl-4-diisopropylaminobutane;
1,1-Diphenyl-4-n-butylaminobutane;
1,1-Diphenyl-4-di-n-butylaminobutane;
1,1-Diphenyl-4-tert.-butylaminobutane;
4,4-Diphenylbutyldiisopropylammonium chloride;
4,4-Diphenylbutyldiisopropylammonium acetate;
4,4-Diphenylbutyldiisopropylmethylammonium methanesulfate;
4,4-Diphenylbutylpropylammonium iodide; and the like.

As hereinbefore indicated, alkylene diamines have previously been prepared and evaluated as antiarrhythmic agents. Of these derivatives, the most potent antiarrhythmic agent appears to be N-phenyl-N-(2-indanyl)-N',N'-diethylpropylenediamine. One might expect the 1,1-diphenyl-4-diethylaminobutane to be the most potent antiarrhythmic agent of the diphenylbutylamines. This has been found not to be the case; in contrast, the diethylamino derivative has poor antiarrhythmic activity when compared to the compounds of this invention.

The diphenylbutylamines of this invention can be formulated for convenient administration, such as oral or parenteral administration for example. The compounds of this invention will generally be administered in amounts ranging from about 4 to 20 mg. per Kg. of body weight once or twice each day. The compounds of this invention can be admixed with pharmaceutically acceptable excipients, diluents or carriers, and formulated as tablets, capsules, or as a solution for easy oral administration. Typical excipients and diluents commonly employed in such pharmaceutical formulations include sucrose, starch powder, microcrystalline cellulose, dextrose, sorbital, propylene glycol, calcium phosphate, gelatin, and the like. Generally, a 0.1 to 1.0-percent by weight solution of a compound of this invention in a carrier such as mannitol or dextrose is preferred. The compounds can be formulated for parenteral administration with suitable carriers or diluents such as saline solution for example. If desired, the active ingredient of this invention can be admixed with one or more active antiarrhythmic agents, such as procainamide or lidocaine for instance. The compounds of this invention are best suited for the therapeutic, as well as prophylactic control of heart arrhythmias.

The following detailed examples are presented to more fully illustrate the invention. The examples should not, however, be construed as limiting the invention to the particular compounds described therein.

EXAMPLE 1

1,1-Diphenyl-4-n-propylaminobutane

A solution of 15.0 g. of 1,1-diphenyl-4-chlorobutane and 35cc. of propylamine in 75 cc. of ethyl alcohol was heated in a sealed bomb at 100° C. for 16 hours. After cooling the reaction mixture to about 25° C., the solvent was removed under reduced pressure. The product was dissolved in 100 cc. of diethyl ether and washed with 5 N sodium hydroxide, and the product was extracted with 2 N hydrochloric acid. The aqueous acidic extracts were combined and the pH was adjusted to 11 by the addition of 5 N sodium hydroxide. The product was insoluble in the aqueous basic solution and was extracted therefrom into diethyl ether. The ethereal extracts were combined, washed with water and dried, and hydrogen chloride gas was added to the ethereal solution. The hydrochloride salt of 1,1-diphenyl-4-n-propylaminobutane crystallized and was collected by filtration. m.p. 94°–96° C.

Analysis Calc. for $C_{19}H_{26}NCl$. Theory: C, 75.10; H, 8.62; N, 4.61; Cl, 11.67. Found: C, 74.87; H, 8.40; N, 4.86; Cl, 11.62.

EXAMPLES 2–5

Following the procedure set forth in Example 1, the following compounds were prepared from the corresponding amine and diphenylbutylchloride:

1,1-Diphenyl-4-isopropylaminobutane hydrochloride; m.p. 160°–163° C.

Analysis Calc. for $C_{19}H_{26}NCl$. Theory: C, 75.10; H, 8.62; N, 4.61; Cl 11.67. Found: C, 74.91; H, 8.39; N, 4.80; Cl, 11.66.

1,1-Diphenyl-4-diisopropylaminobutane hydrochloride m.p. 130°–135° C.

Analysis Calc. for $C_{22}H_{32}NCl$. Theory: C, 76.38; H, 9.32; N, 4.05; Cl, 10.25. Found: C, 76.61; H, 9.09; N, 4.00; Cl, 10.46.

1,1-Diphenyl-4-di-n-butylaminobutane

Analysis Calc. for $C_{24}H_{35}N$ Theory: C, 85.40; H, 10.45; N, 4.13. Found: C, 85.60; H, 10.71; N, 3.95.

1,1-Diphenyl-4-tert.-butylaminobutane hydrochloride; m.p. 208°–210° C.

Analysis Calc. for $C_{20}H_{28}NCl$. Theory: C, 75.56; H, 8.88; N, 4.41; Cl, 11.15. Found: C, 75.51; H, 8.84; N, 4.13; Cl, 11.41.

I claim:

1. The compound of the formula

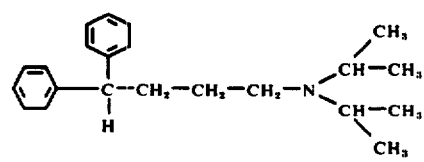

and the physiologically tolerable salts thereof.

2. The acid addition salt of the compound of claim 1

* * * * *